(12) United States Patent
Muda et al.

(10) Patent No.: US 7,740,862 B2
(45) Date of Patent: Jun. 22, 2010

(54) FSH MUTANTS

(75) Inventors: Marco Muda, Cambridge, MA (US);
Xuliang Jiang, Braintree, MA (US);
Sean D. McKenna, Duxbury, MA (US)

(73) Assignee: Merck Serono S.A., Coinsins, Vaud (CH)

( * ) Notice: Subject to any disclaimer, the term of this patent is extended or adjusted under 35 U.S.C. 154(b) by 21 days.

(21) Appl. No.: 12/096,125

(22) PCT Filed: Dec. 21, 2006

(86) PCT No.: PCT/US2006/048898

§ 371 (c)(1),
(2), (4) Date: Jun. 4, 2008

(87) PCT Pub. No.: WO2008/010840

PCT Pub. Date: Jan. 24, 2008

(65) Prior Publication Data

US 2009/0018070 A1 Jan. 15, 2009

Related U.S. Application Data

(60) Provisional application No. 60/753,637, filed on Dec. 22, 2005.

(51) Int. Cl.
*A61K 39/00* (2006.01)
*A61K 38/00* (2006.01)
*A01N 37/18* (2006.01)
*C07K 1/00* (2006.01)
*C07K 14/00* (2006.01)

(52) U.S. Cl. .................. 424/198.1; 514/2; 530/397; 530/398; 530/300

(58) Field of Classification Search .............. None
See application file for complete search history.

(56) References Cited

U.S. PATENT DOCUMENTS 5,864,488 A * 1/1999 Isaacs et al. ............ 702/27

FOREIGN PATENT DOCUMENTS

| WO | WO 91/16922 A1 | 11/1991 |
| WO | WO 01/58493 A1 | 8/2001 |
| WO | WO 2004/050679 A2 | 6/2004 |
| WO | WO 2005/020934 A2 | 3/2005 |
| WO | WO 2007/084441 A2 | 7/2007 |

OTHER PUBLICATIONS

Furuhashi, M. et al. "Effect of additional N-glycosylation signal in the N-terminal region on intracellular function of the human gonadotropin α-subunit" *Endocrine Journal*, Jun. 2003, pp. 245-253, vol. 50, No. 3.

Perlman, S. et al. "Glycosylation of an N-terminal extension prolongs the half-life and increases the in-vivo activity of follicle stimulating hormone" *Journal of Clinical Endocrinology and Metabolism*, Jul. 2003, pp. 3227-3235, vol. 88, No. 7.

Weenen, C. et al. "Long-acting follicle-stimulating hormone analogs containing N-linked glycosylation exhibited increased bioactivity compared with O-linked analogs in female rates" *Journal of Clinical Endocrinology and Metabolism*, Oct. 2004, pp. 5204-5212, vol. 89, No. 10.

Chappel, S. et al. "Follicle stimulating hormone and its receptor: future perspectives" *Human Reproduction*, 1998, pp. 18-35 and 47-51, vol. 12, Supplement No. 3.

Grossman, M. et al. "Site-Directed Mutagenesis of Amino Acids 33-44 of the Common α-Subunit Reveals Different Structural Requirements for Heterodimer Expression among the Glycoprotein Hormones and Suggests that cyclic Adenosine 3',5'-Monophosphate Production and Growth Promotion are Potentially Dissociable Functions of Human Thyrotropin" *Molecular Endocrinology*, 1996, pp. 769-779, vol. 10, No. 6.

Klein, J. et al. "Development and characterization of a long-acting recombinant hFSH agonist" *Human Reproduction*, pp. 50-56, 2003, vol. 18, No. 1.

Liu, C. et al. "Site-directed Alanine Mutagenesis of Phe$^{33}$, Arg$^{35}$, and Arg$^{42}$-Ser$^{43}$-Lys$^{44}$ in the Human Gonadotropin α-Subunit" *The Journal of Biological Chemistry*, Oct. 15, 1993, vol. 268, No. 29.

Valove, F.M. et al. "Receptor Binding and Signal Transduction are Dissociable Functions Requiring Different Sites on Follicle Stimulating Hormone" *Endocrinology*, 1994, pp. 2657-2661, vol. 135, No. 6.

Roth, K.E. et al. "Scanning-alanine mutagenesis of long loop residues 33-53 in follicle stimulating hormone beta subunit" *Molecular and Cellular Endocrinology*, 1995, pp. 143-149, vol. 109.

Bishop, L.A. et al. "Both of the β-Subunit Carbohydrate Residues of Follicle-Stimulating Hormone Determine the Metabolic Clearance Rate and in Vivo Potency" *Endocrinology*, 1995, pp. 2635-2640, vol. 136, No. 6.

D'Antonio, M. et al. "Biological characterization of recombinant human follicle stimulating hormone isoforms" *Human Reproduction*, 1999, pp. 1160-1167, vol. 14, No. 5.

Galway, A. B. et al. "In Vitro and in Vivo Bioactivity of Recombinant Human Follicle-Stimulating Hormone and Partially Deglycosylated Variants Secreted by Transfected Eukaryotic Cell Lines" *Endocrinology*, 1990, pp. 93-100, vol. 127.

Yoo, J. et al. "COOH-terminal Amino Acids of the α Subunit Play Common and Different Roles in Human Choriogonadotropin and Follitropin" *The Journal of Biological Chemistry*, Jun. 25, 1993, pp. 13034-13042, vol. 268, No. 18.

* cited by examiner

*Primary Examiner*—Gary B Nickol
*Assistant Examiner*—Shulamith H Shafer
(74) *Attorney, Agent, or Firm*—Saliwanchik, Lloyd & Saliwanchik

(57) ABSTRACT

FSH mutants with increased glycosylation and longer half-lives are described. The use of FSH mutants for inducing folliculogenesis in human patients is also described.

10 Claims, 2 Drawing Sheets

FIGURE 1

```
               10         20         30         40         50
                |          |          |          |          |
alpha      APD----VQDCPECTLQENPFFSQPGAPILQCMGCCFSRAYPTPLRSKKTMLVQKNVTSE
GNFT       APDGNFTVQDCPECTLQENPFFSQPGAPILQCMGCCFSRAYPTPLRSKKTMLVQKNVTSE
GNRT       APDGNRTVQDCPECTLQENPFFSQPGAPILQCMGCCFSRAYPTPLRSKKTMLVQKNVTSE 60         70         80         90
                |          |          |          |
alpha      STCCVAKSYNRVTVMGGFKVENHTACHCSTCYYHKS
GNFT       STCCVAKSYNRVTVMGGFKVENHTACHCSTCYYHKS
GNRT       STCCVAKSYNRVTVMGGFKVENHTACHCSTCYYHKS
```

FSH MUTANTS

CROSS-REFERENCE TO RELATED APPLICATION

This application is the U.S. national stage application of International Patent Application No. PCT/US2006/048898, filed Dec. 21, 2006, which claims the benefit of U.S. Provisional Patent Application No. 60/753,637, filed Dec. 22, 2005, the disclosures of which are hereby incorporated by reference in their entireties, including all figures, tables and amino acid or nucleic acid sequences.

BACKGROUND OF THE INVENTION

1. Field of the Invention

The present invention relates to human reproduction. More specifically, the present invention relates to fertilization therapies.

2. Description of Related Art a. Gonadotropins

Follicle stimulating hormone (FSH) is a member of the family of gonadotrophins that play key roles in human fertility. The gonadotrophins, which also include luteinising hormone (LH) and chorionic gonadotrophin (CG), are heterodimers, each consisting of a common α-subunit (92 amino acids) and a unique β-subunit (111 amino acids in FSH). The amino acid sequences of the mature forms of the α- and β-subunits of FSH are shown in SEQ ID NO:1 and SEQ ID NO:2, respectively.

Human FSH has been isolated from pituitary glands and from postmenopausal urine (EP 322,438) and has been produced recombinantly in mammalian cells (U.S. Pat. Nos. 5,639,640, 5,156,957, 4,923,805, 4,840,896, 5,767,251, EP 211,894 and EP 521,586). The latter references also disclose the human FSH β-subunit gene. U.S. Pat. No. 5,405,945 discloses a modified human α-subunit gene comprising only one intron.

Liu et al., J Biol Chem 1993, 15; 268 (2): 21613-7, Grossmann et al., Mol Endocrinol 1996 10 (6): 769-79, Roth and Dias (Mol Cell Endocrinol 1995 1; 109 (2): 143-9, Valove et al., Endocrinology 1994; 135 (6): 2657-61, Yoo et al., J Biol Chem 1993 25; 268 (18): 13034-42), U.S. Pat. No. 5,508,261 and Chappel et al., 1998, Human Reproduction, 13 (3): 1835 disclose various structure-function relationship studies and identify amino acid residues involved in receptor binding and activation and in dimerization of FSH.

b. Use of Gonadotropins in Assisted Reproductive Techniques

The gonadotrophins play crucial roles in the reproductive cycle, and their use in exogenous therapies is essential for assisted reproductive techniques (ART), such as in vitro fertilization (IVF), IVF in conjunction with intracytoplasmic sperm injection (IVF/ICSI) and embryo transfer (ET), as well as for ovulation induction (OI) in anovulatory patients undergoing in vivo fertilization either naturally or through intrauterine insemination (IUI).

U.S. Pat. No. 4,589,402 and U.S. Pat. No. 4,845,077 disclose purified human FSH which is free of LH and the use thereof for in vitro fertilization. EP 322 438 discloses a protein with at least 6200 U/mg FSH activity which is substantially free of LH activity, and wherein the FSH α-subunit and the β-subunit, respectively, may be wild type or specified truncated forms thereof.

Prolonged therapy is necessary to achieve a therapeutic effect, typically for 8-10 consecutive days and sometimes up to 21 days to stimulate folliculogenesis in women, and for up to 18 months in hypogonadotrophic males to induce spermatogenesis. Recombinant hFSH is typically administered as an i.m. or s.c. daily injection, with consequent discomfort and potential for local injection site reaction. Decreasing the frequency of administration would facilitate therapy and render gonadotrophin administration more convenient, more tolerable and patient-friendly.

c. Glycosylation of FSH

The gonadotrophins are glycoproteins, with each sub-unit having asparagine-linked (N-linked) oligosaccharide side chains that are important for in vivo activity and function. Carbohydrate addition (glycosylation) to polypeptides is a post-translational event that results in the addition of sugar chains to specific asparagine (N-linked) or serine/threonine (O-linked) amino acids. In contrast to the invariant amino acid sequence of the protein portion of glycoproteins, the carbohydrate structures are variable, a feature referred to as microheterogeneity. For example, N-glycosylation sites on the same protein may contain different carbohydrate structures. Furthermore, even at the same glycosylation site on a given glycoprotein, different carbohydrate structures may be found. This heterogeneity is a consequence of the non-template-directed synthesis of carbohydrates.

N-glycosylation of proteins occurs specifically at the consensus pattern Asn-Xaa-Ser/Thr, and to a lesser extent at the consensus pattern Asn-Xaa-Cys, where Xaa can be any amino acid residue. However, the presence of a consensus tripeptide is not sufficient to insure that an asparagine residue will be glycosylated. For example, N-glycosylation of the Asn-Pro-Ser/Thr sequence occurs at a rate 50-times lower than the other consensus patterns of Asn-Xaa-Ser/Thr.

Human FSH contains four N-linked glycosylation sites: two on the common α-subunit at positions 52 and 78 and two on the β-subunit at positions 7 and 24. Carbohydrates attached to the α-subunit of FSH are critical for dimer assembly, integrity, secretion and signal transduction, whereas β-subunit carbohydrates are important for dimer assembly, secretion and clearance of the heterodimer from the circulation.

Galway et al., Endocrinology 1990; 127 (1): 93-100 demonstrate that FSH variants produced in a N-acetylglucosamine transferase-I CHO cell line or a CHO cell line defective in sialic acid transport are as active as FSH secreted by wild type cells or purified pituitary FSH in vitro, but lacked in vivo activity, presumably due to rapid clearance of the inadequately glycosylated variants in serum. D'Antonio et al., Human Reprod 1999; 14 (5): 1160-7 describe various FSH isoforms circulating in the blood stream. The isoforms have identical amino acid sequences, but differ in their extent of post-translational modification. It was found that the less acidic isoform group had a faster in vivo clearance as compared with the acidic isoform group, possibly due to differences in the sialic acid content between the isoforms. Moreover, Bishop et al. Endocrinology 1995; 136 (6): 2635-40 conclude that circulatory half-life appears to be the primary determinant of in vivo activity. These observations led to the hypothesis that the half-life of FSH could be increased by introducing additional glycosylation sites to increase the sialic acid content of the polypeptide.

d. FSH Variants

FSH agonists with increased half-lives have been developed by fusing the carboxyterminal peptide of hCG (CTP) to native recombinant human FSH (rhFSH). The CTP moiety consists of amino acids 112-118 to 145 with four O-linked glycosylation sites located at positions 121, 127, 132 and 138. U.S. Pat. Nos. 5,338,835 and 5,585,345 disclose a modified FSH β-subunit extended at the C-terminal Glu with the CTP moiety of hCG. The resulting modified analogue is stated to have the biological activity of native FSH, but a prolonged circulating half-life. U.S. Pat. No. 5,405,945 discloses that the carboxy terminal portion of the hCG α-subunit or a variant thereof has significant effects on the clearance of CG, FSH, and LH.

U.S. Pat. No. 5,883,073 discloses single-chain proteins comprised of two α-subunits with agonist or antagonist activity for CG, TSH, LH and FSH. U.S. Pat. No. 5,508,261 discloses heterodimeric polypeptides having binding affinity to LH and FSH receptors comprising a glycoprotein hormone α-subunit and a non-naturally occurring β-subunit polypeptide, wherein the β-subunit polypeptide is a chain of amino acids comprising four joined subsequences, each of which is selected from a list of specific sequences. Klein et al. (2003) discloses a single chain analogue of FSH with an increased half-life, wherein the α- and β-subunits are linked by an oligopeptide containing two N-linked glycosylation sites.

WO 01/58493 discloses 77 mutations that may be made in the α-subunit of FSH and 51 mutations that may be made in the β-subunit of FSH in an attempt to improve the in vivo half-life of FSH. In addition, WO 01/58493 discloses that one or more glycosylation sites may be added to the N-terminus of FSH to improve its half-life or inserted at various sites within the FSH polypeptide. WO 01/58493, while describing that glycosylation sites may be inserted into the FSH polypeptide, it provided no guidance as the specific site(s) where one could insert a glycosylation site and maintain FSH activity. WO 01/58493 further discloses that the mutant α- and β-subunits may be used individually (1 additional glycosylation site) or in combination (2 additional glycosylation sites). The 128 candidate mutants were identified by using 50 models of the 3D structure of FSH that were generated based solely on the structure of hCG and a sequence alignment of FSH and hCG despite only 32% identity between the β-subunits of hCG and FSH. WO 01/58493 does not disclose the production or testing of any α- or β-subunits of FSH where a glycosylation site was introduced by site directed mutagenesis.

WO 05/020934 discloses GM1, with mutations in both the α- and β-subunits of FSH, including a double mutation at β E55N/V57T, i.e., the E residue at amino acid position 55 mutated to N and the V residue at amino acid position 57 mutated to T. The amino acid sequence of β E55N/V57T is shown in SEQ ID NO:3.

A clinical need exists for a product which provides part or all of the therapeutically relevant effects of FSH, and which may be administered at less frequent intervals as compared to currently available FSH products, and which preferably provides a more stable level of circulating FSH activity as compared to that obtainable by current treatment.

The present invention is directed to such products as well as the means of making such products.

SUMMARY

The present invention relates to mutant FSH molecules, wherein the FSH α-subunit comprises a sequence selected from the group consisting of SEQ ID NOS:4-5 and wherein the FSH β-subunit comprises SEQ ID NO: 3. The FSH may be N-glycosylated at 0, 1, 2, 3, 4, 5 or 6 asparagine residues of said mutant FSH. In one embodiment N5 of the mutant α-subunit of SEQ ID NO:4 may be glycosylated. In another embodiment N5 of the mutant α-subunit of SEQ ID NO:5 may be glycosylated. In one embodiment N55 of the mutant β-subunit of SEQ ID NO:3 may be glycosylated.

The present invention also relates to isolated DNA molecules encoding FSH α-subunit mutants selected from the group consisting of SEQ ID NOS:4-5. The present invention also relates to an isolated DNA encoding an FSH β-subunit comprising the sequence of SEQ ID NO:3.

The present invention also relates to a vector comprising DNA encoding an FSH α-subunit mutant selected from the group consisting of SEQ ID NOS:4-5. The vector may be an expression vector.

The present invention also relates to a vector comprising DNA encoding an FSH β-subunit mutant comprising the sequence of SEQ ID NO:3. The vector may be an expression vector.

The present invention also relates to a vector comprising a first DNA and a second DNA, wherein the first DNA encodes an FSH α-subunit mutant selected from the group consisting of SEQ ID NOS:4-5 and wherein the second DNA encodes an FSH β-subunit mutant comprising the sequence of SEQ ID NO:3. The vector may be an expression vector.

The present invention also relates to a cell comprising a vector comprising DNA encoding an FSH α-subunit mutant selected from the group consisting of SEQ ID NOS:4-5. The vector may be an expression vector. The cell may be a mammalian cell, e.g., a CHO cell.

The present invention also relates to a cell comprising a vector comprising DNA encoding an FSH β-subunit mutant comprising the sequence of SEQ ID NO:3. The vector may be an expression vector. The cell may be a mammalian cell, e.g., a CHO cell.

The present invention also relates to a cell comprising a vector comprising a first DNA and a second DNA, wherein the first DNA encodes an FSH α-subunit mutant selected from the group consisting of SEQ ID NOS:4-5 and wherein the second DNA encodes an FSH β-subunit mutant comprising the sequence of SEQ ID NO:3. The vector may be an expression vector. The cell may be a mammalian cell, e.g., a CHO cell.

The present invention also relates to a cell comprising a first and a second vector, wherein the first vector comprises DNA encoding an FSH α-subunit mutant selected from the group consisting of SEQ ID NOS:4-5 and the second vector comprises DNA encoding an FSH β-subunit mutant comprising the sequence of SEQ ID NO:3. The vector(s) may be an expression vector. The cell may be a mammalian cell, e.g., a CHO cell.

The present invention also relates to a method for producing an FSH mutant comprising culturing mammalian cells capable of glycosylating proteins, wherein said cells comprise a first expression vector comprising DNA encoding an FSH α-subunit mutant selected from the group consisting of SEQ ID NOS:4-5 and a second expression vector comprising DNA encoding an FSH β-subunit mutant comprising the sequence of SEQ ID NO:3. In another embodiment of the present invention said cells comprise a single vector comprising DNA encoding an FSH α-subunit mutant selected from the group consisting of SEQ ID NOS:4-5 and further comprising DNA encoding an FSH β-subunit mutant comprising the sequence of SEQ ID NO:3.

The present invention also relates to a composition comprising an FSH mutant and a pharmaceutically acceptable carrier or excipient, wherein the FSH α-subunit comprises a sequence selected from the group consisting of SEQ ID NOS: 4-5 and wherein the FSH β-subunit comprises SEQ ID NO:3.

The present invention also relates to a method of treating an infertile mammal, comprising administering to a mammal in need thereof an effective amount of a mutant FSH mutant, wherein the FSH α-subunit comprises a sequence selected from the group consisting of SEQ ID NOS:4-5 and wherein the FSH β-subunit comprises SEQ ID NO:3.

The present invention also relates to a method of stimulating folliculogenesis in a mammal, comprising administering to a mammal in need thereof an effective amount of a mutant FSH, wherein the FSH α-subunit comprises a sequence selected from the group consisting of SEQ ID NOS:4-5 and wherein the FSH β-subunit comprises SEQ ID NO:3. The present invention also relates to a method of inducing ovarian hyperstimulation in a mammal, comprising administering to a mammal in need thereof an effective amount of a mutant FSH, wherein the FSH α-subunit comprises a sequence selected from the group consisting of SEQ ID NOS:4-5 and wherein the FSH β-subunit comprises SEQ ID NO:3.

BRIEF DESCRIPTION OF THE DRAWINGS

FIG. 1 shows an alignment of the GNFT (SEQ ID NO: 4), and GNRT (SEQ ID NO:5) α-subunit mutants to the human α-subunit of FSH (SEQ ID NO: 1). The residue numbers refer to the human α-subunit of FSH (SEQ ID NO: 1) with 1 being the first amino acid of the mature polypeptide.

DETAILED DESCRIPTION OF THE INVENTION

Figure 2:
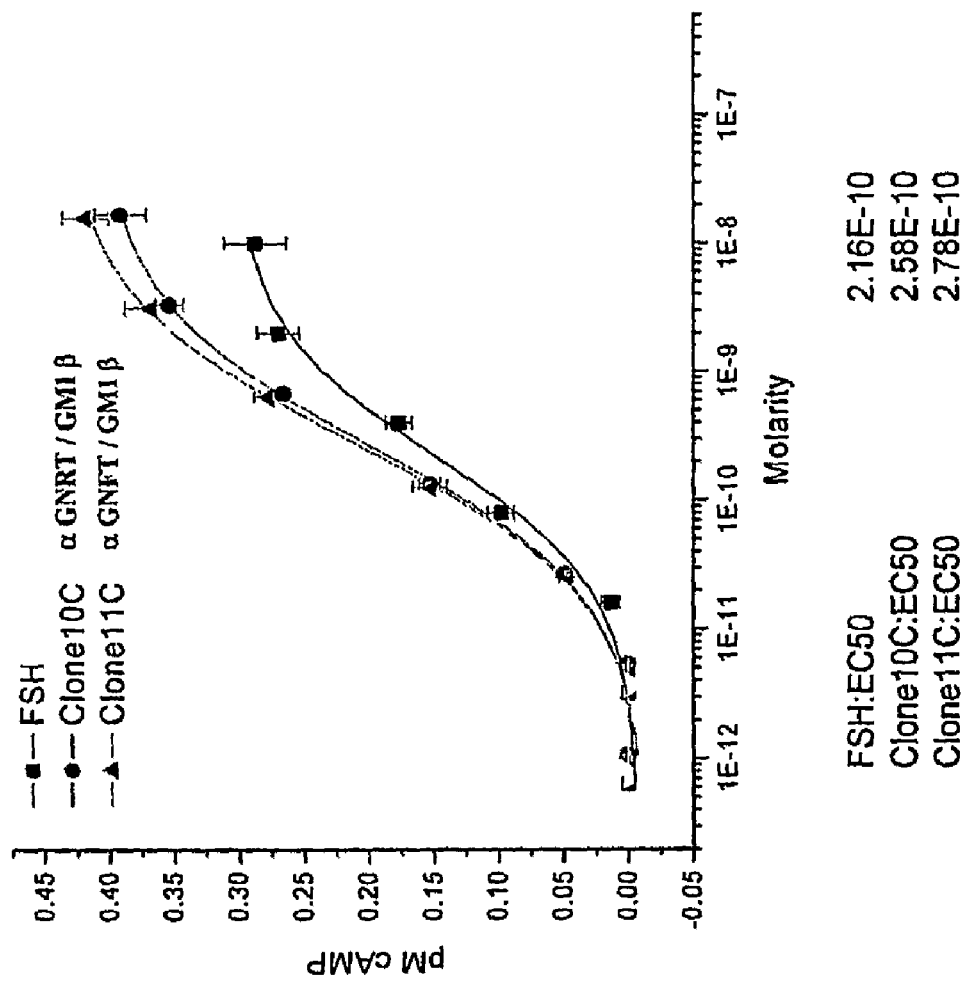
FIG. 2 shows a dose-response curve for the mutant FSH α-subunits compared to wild-type FSH. Clone 10c-α GNRT/GM1 β. Clone 11c-α GNFT/GM1β.

While it has been shown that increasing the carbohydrate content of FSH may lead to increased in vivo half-life, improving the half-life of FSH is more complicated than simply adding additional glycosylation sites. While a glycosylation consensus sequence is necessary for carbohydrate addition, it is not sufficient to ensure that a carbohydrate addition site will be utilized. Other factors, such as the local protein folding and conformation during biosynthesis, determine whether an oligosaccharide is attached at a given consensus sequence site. In addition, in order for the additional glycosylation to lead to an increase in the in vivo half-life the consensus sequence must be in a position such that glycosylation of the site does not interfere with receptor binding, or compromise the folding, conformation or stability of the glycoprotein. To this point, FSH analogues with increased half-lives have primarily been limited to fusion proteins wherein the fused portion of the polypeptide included additional glycosylation sites.

1. Mutant FSH

An FSH mutant is provided that has been modified to create additional glycosylation recognition sites. The α-subunit of the FSH mutant may have one of the following mutations, compared to the wild-type α-subunit: an insertion of the amino acid sequence GNFT between amino acid residues 3 and 4 of the wild type α-subunit or an insertion of the amino acid sequence GNRT between amino acid residues 3 and 4 of the wild type α-subunit. A mutant FSH may comprise any of the above mutant α-subunits in combination with mutant β-subunit, e.g. β GM1 containing the following mutation: E55N/V57T. One or more of the additional glycosylation sites of the recombinant FSH may be glycosylated. The one or more additional glycosylation sites of the mutant FSH may be glycosylated in vitro or in vivo. As used herein, the term "GNFT mutant" refers to a mutant FSH comprising an α subunit as set out in SEQ ID NO:4 and a β subunit as set out in SEQ ID NO:3. As used herein, the term "GNRT mutant" refers to a mutant FSH comprising an α subunit as set out in SEQ ID NO:5 and a β subunit as set out in SEQ ID NO:3.

The FSH mutant may be produced by any suitable method known in the art. These methods include the construction of nucleotide sequences encoding the respective FSH mutants and expressing the amino acid sequence in a suitable transfected host. The FSH mutant may also be produced by chemical synthesis or by a combination of chemical synthesis and recombinant DNA technology.

The FSH mutant may comprise the α- and β-subunits of FSH in the form of two separate polypeptide chains, where the two chains dimerize in vivo so as to form a dimeric polypeptide, or it may comprise a single chain construct comprising the two subunits covalently linked by a peptide bond or a peptide linker. The amino acid residues of the linker peptide may exhibit properties that do not interfere significantly with the activity of the FSH mutant.

The FSH mutant may have an increased half-life compared to wild type FSH. The FSH mutant may also have increased stability compared to wild type FSH. The FSH mutant may comprise oligosaccharides at 0, 1, 2, 3, 4, 5 or 6 of the N-linked glycosylation sites. A population of FSH mutants is also provided, which may comprise one or more FSH mutant isoforms, wherein each isoform comprises oligosaccharides at 0, 1, 2, 3, 4, 5 or 6 of the N-linked glycosylation sites.

The nucleotide sequence encoding the α- or β-subunits of the FSH mutant may be constructed by isolating or synthesizing a nucleotide sequence encoding the parent FSH subunit, such as the hFSH-alpha or hFSH-beta with the amino acid sequences shown in SEQ ID NOS: 1 and 2, respectively. The nucleotide sequence may then be changed so as to effect the substitution o rinsertion of the relevant amino acid residues. The nucleotide sequence can be modified by site directed mutagenesis. In the alternative, the nucleotide sequence may be prepared by chemical synthesis, wherein oligonucleotides are designed based on the specific amino acid sequence of the FSH mutant.

The nucleotide sequence encoding the polypeptide may be inserted into a recombinant vector and operably linked to a control sequence necessary for expression of the polypeptide in the desired transfected host cell. The control sequences may be any component that is necessary or advantageous for the expression of a polypeptide. Examples of suitable control sequences for directing transcription in mammalian cells include the early and late promoters of SV40 and adenovirus, e.g. the adenovirus 2 major late promoter, the MT-1 (metallothionein gene) promoter and the human cytomegalovirus immediate-early gene promoter (CMV).

One of skill in the art may make a selection among these vectors, expression control sequences and hosts without undue experimentation. The recombinant vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector may be an expression vector in which the nucleotide sequence encoding the polypeptide of the invention is operably linked to additional segments required for transcription of the nucleotide sequence. The vector may be derived from plasmid or viral DNA. A number of suitable expression vectors for expression in the host cells mentioned herein are commercially available or described in the literature The recombinant vector may further comprise a DNA sequence enabling the vector to replicate in the host cell in question. An example of such a sequence, (when the host cell is a mammalian cell) is the SV40 origin of replication. The vector may also comprise a selectable marker, e.g. a gene whose product complements a defect in the host cell, such as the gene coding for dihydrofolate reductase (DHFR) or one which confers resistance to a drug, e.g. ampicillin, kanamycin, tetracycline chloramphenicol, neomycin, hygromycin or methotrexate.

The vector may also comprise an amplifiable gene, such as DHFR, such that cells having multiple copies of the amplifiable gene and flanking sequences, including the mutant FSH DNA, can be selected for on appropriate media.

Also provided is a DNA encoding an α-subunit of the FSH mutant. The nucleotide sequence encoding the alpha and beta subunits of the FSH mutant, whether prepared by site-directed mutagenesis, synthesis, PCR or other methods, may optionally also include a nucleotide sequence that encodes a signal peptide. The signal peptide may be present when the polypeptide is to be secreted from the cells in which it is expressed. Such signal peptide, if present, may be one recognized by the cell chosen for expression of the polypeptide. The signal peptide may be homologous (e.g. be that normally associated with a hFSH subunit) or heterologous (i.e. originating from another source than hFSH) to the polypeptide or may be homologous or heterologous to the host cell, i.e. be a signal peptide normally expressed from the host cell or one which is not normally expressed from the host cell.

Any suitable host may be used to produce the polypeptides, including bacteria, fungi (including yeasts), plant, insect, mammal, or other appropriate animal cells or cell lines, as well as transgenic animals or plants. Examples of suitable mammalian host cells include Chinese hamster ovary (CHO) cell lines, (e.g. CHO-KL; ATCC CCL-61), Green Monkey cell lines (COS) (e.g. COS 1 (ATCC CRL-1650), COS 7 (ATCC CRL-1651)); mouse cells (e.g. NSIO), Baby Hamster Kidney (BI-EK) cell lines (e.g. ATCC CRL-1632 or ATCC CCL-10), and human cells (e.g. BEK 293 (ATCC CRL-1573)), as well as plant cells in tissue culture. Additional suitable cell lines are known in the art and available from public depositories such as the American Type Culture Collection, USA. Methods for introducing exogenous DNA into mammalian host cells include calcium phosphate-mediated transfection, electroporation, DEAE-dextran mediated transfection, liposome-mediated transfection and viral vectors.

Cells may be cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g. in catalogues of the American Type Culture Collection). If the polypeptide is secreted into the nutrient medium, it can be recovered directly from the medium. If the polypeptide is not secreted, it can be recovered from cell lysates. One method of high-yield production of the FSH mutants of the invention is through the use of dihydrofolate reductase (DHFR) amplification in DHFR-deficient CHO cells, by the use of successively increasing levels of methotrexate as described in U.S. Pat. No. 4,889,803.

The resulting mutant FSH polypeptide may be recovered by methods known in the art. For example, it may be recovered from the nutrient medium by conventional procedures including, but not limited to, centrifugation, filtration, extraction, spray drying, evaporation, or precipitation. The mutant FSH polypeptides may be purified by a variety of procedures known in the art including, but not limited to, chromatography (e.g. ion exchange, affinity, hydrophobic, chromatofocusing, and size exclusion), electrophoretic procedures (e.g. preparative isoelectric focusing), differential solubility (e.g. ammonium sulfate precipitation), SDS-PAGE, or extraction.

Also provided is a pharmaceutical composition comprising the FSH mutant. Such pharmaceutical composition may be used to stimulate folliculogenesis, for example in conjunction with ovulation induction or assisted reproductive techniques (ART). Because the FSH mutant of the present invention may be effective in inducing multiple follicles to develop and mature, it may be particularly suitable for use in ART, in which it is desired to collect multiple oocytes.

The FSH mutant may be used to induce mono-folliculogenesis for OI, or paucifolliculogenesis (up to about three follicles) for IUI, for in vivo fertilization. Mono-folliculogenesis can also be attained with a reduced dose of the FSH mutant, or less frequent dosing as compared with conventional FSH preparations. For example, in OI an FSH preparation of the invention may be administered at 225-400 IU every three days, or lower doses, depending on the patient response. Patient response may be followed by sonography.

The FSH mutant of the invention may be used in a controlled ovarian hyperstimulation (COH) regimen. Standard regimens for COH include a down-regulation phase in which endogenous luteinising hormone (LH) is down-regulated by administration of a gonadotrophin releasing hormone (GnRH) agonist followed by a stimulatory phase in which follicular development (folliculogenesis) is induced by daily administration of follicle stimulating hormone (FSH), usually at about 150-225 IU/day. Alternatively stimulation may be started with FSH after spontaneous or induced menstruation, followed by administration of a GnRH-antagonist (typically starting around day six of the stimulatory phase). When there are at least 3 follicles>16 mm (one of 18 mm), a single bolus of hCG (5-10,000 IU) may be given to mimic the natural LH surge and induce ovulation. Oocyte recovery may be timed for 36-38 hours after the hCG injection.

The FSH mutant may also be used for OI and IUI. For example, FSH stimulation may be started after spontaneous or induced menstruation, at a daily dose of 75-150 IU. When 1 or 3 follicles have reached a diameter of at least 16 mm, a single bolus of hCG may be administered to induce ovulation. Insemination may be performed in vivo, by regular intercourse or IUI.

Because the FSH mutant may have an increased half-life with respect to wild type FSH preparations, regimens such as that described above may employ lower IU doses of FSH, and/or may be modified by decreasing the FSH stimulation period, while achieving the same or better response, in terms of number and viability of follicles. For example, adequate folliculogenesis may be achieved with daily doses of at or about 50-150, 50-100 or 50-75 IU FSH. Dosing of FSH may be on a daily or semi-daily basis. The dosing period may be less than or about 14, 12, 11 or 10 days. For OI, the FSH mutant preparation may be administered at doses from 25-150 or 50-125 IU FSH/day. For the treatment of male infertility, an FSH mutant preparation may be administered at 3×150 to 300 IU/week until spermatogenesis reaches levels adequate for insemination, either through regular intercourse or ART techniques.

Because of the longer half-life of the mutant FSH, it may be administered as a long-acting preparation, which may be administered less frequently than every two days. Conventional FSH may be administered at or about 300 IU on every second day, while achieving similar results to administration every day at or about 150 IU. The mutant FSH may be administered every 3, 4, 5, 6 or 7 days, while achieving similar or better results than daily administration of conventional FSH.

The FSH mutant may be used for the manufacture of a medicament for treatment of diseases, disorders or conditions. In another aspect, the polypeptide or the pharmaceutical composition according to the invention is used in a method of treating a mammal, in particular a human, comprising administering to the mammal in need thereof such polypeptide or pharmaceutical composition.

It will be apparent to those of skill in the art that an effective amount of a polypeptide, preparation or composition depends, inter alia, upon the disease, the dose, the administration schedule, whether the polypeptide or preparation or composition is administered alone or in conjunction with other therapeutic agents, the serum half-life of the compositions, and the general health of the patient. Typically, an effective dose of the preparation or composition is sufficient to ensure a therapeutic effect.

The FSH mutant may be administered in a composition including one or more pharmaceutically acceptable carriers or excipients. "Pharmaceutically acceptable" means a carrier or excipient that does not cause any untoward effects in patients to whom it is administered. Such pharmaceutically acceptable carriers and excipients are well known in the art, and the polypeptide may be formulated into pharmaceutical compositions by well-known methods (see e.g. Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). Pharmaceutically acceptable excipients that may be used in compositions comprising the polypeptide include, for example, buffering agents, stabilizing agents, preservatives, isotonifiers, nonionic surfactants or detergents "wetting agents"), antioxidants, bulking agents or fillers, chelating agents and cosolvents.

The pharmaceutical composition comprising the FSH mutant may be formulated in a variety of forms, including liquids, e.g. ready-to-use solutions or suspensions, gels, lyophilized, or any other suitable form, e.g. powder or crystals suitable for preparing a solution. The form of the composition may depend upon the particular indication being treated and will be apparent to one of skill in the art.

The pharmaceutical composition comprising the FSH mutant may be administered intravenously, intramuscularly, intraperitoneally, intradermally, subcutaneously, sublingually, buccally, intranasally, transdermally, by inhalation, or in any other acceptable manner, e.g. using PowderJect or ProLease technology or a pen injection system. The mode of administration may be depend upon the particular indication being treated and will be apparent to one of skill in the art. The composition may be administered subcutaneously, which may allow the patient to conduct self-administration.

The pharmaceutical compositions may be administered in conjunction with other therapeutic agents. These agents may be incorporated as part of the same pharmaceutical composition or may be administered separately from the polypeptides, either concurrently or in accordance with any other acceptable treatment schedule. In addition, the polypeptide, preparation or pharmaceutical composition may be used as an adjunct to other therapies.

The present invention has multiple aspects, illustrated by the following non-limiting examples.

EXAMPLE 1

FSH Mutants

The 3D crystal structure of human FSH was used to identify regions in the FSH molecule where a candidate glycosylation site may be inserted. Two FSH molecules (four subunits) are present in each asymmetric unit of the crystal structure. The two FSH molecules were superimposed and compared, with each residue being visually inspected to identify potential sites where an N-glycosylation site may be inserted that would not disrupt the proper folding of the FSH polypeptide or reduce FSH activity. The crystallographic structure of FSH was combined with the knowledge of the FSH/FSHR receptor interaction to further aid in the selection of potential N-glycosylation sites. The principal design criteria were minimal disruption of 3D structure, minimal disruption of predicted binding and activation sites, and predictable 3D structure compatible with glycosylation. Based on the above criteria, the following two insertion mutants' of the α-subunit of FSH were prepared:

| # | Mutations | SEQ ID NO |
|---|-----------|-----------|
| 1 | GNFT insert | 4 |
| 2 | GNRT insert | 5 |

EXAMPLE 2

Morphological Analysis of FSH Mutants

Aliquots of concentrated culture supernatants from transient expression of FSH α-subunit mutants 1-2 were analyzed by SDS-PAGE under non-reducing conditions that permits the resolution of intact FSH heterodimers from free α- and β-subunits. By comparing the apparent molecular weights of each mutant heterodimer to that of wild-type FSH, one is able to determine whether the mutant FSH is hyperglycosylated relative to wild-type FSH. Briefly, after electrophoresis, proteins were electrophoretically transferred to PVDF and visualized using Serono antibody 9-14 directed against the α-subunit of FSH. As a control, wild-type human FSH, mutant GM1, FSH-CTP and Gonal F were also analyzed. Table 1 shows the apparent molecular weight of the heterodimer formed by the α-subunit mutants and wild-type β-subunit as calculated based on molecular weight standards.

TABLE 1

| Sample | $M_r$ (kDa) | Fold Conc. |
|--------|-------------|------------|
| FSH-CTP | 45.244 | |
| Gonal F | 38.482 | 37x |
| GNFT insert | 49.375 | 36x |
| GNRT insert | 49.172 | 35x |
| GM1 | 46.202 | 40x |
| wt FSH | 45.083 | 36x |

As shown in Table 1, each of the two expressed FSH mutants, i.e. GNFT and GNRT inserts, showed increased glycosylation as evidenced by a shift of the distribution of the apparent molecular weight of the heterodimer compared to wild-type human FSH.

EXAMPLE 3

In Vitro Function of FSH Mutants

In order to determine the activity of the FSH mutants, each mutant was tested for the ability to stimulate cAMP production in a CHO cells line that recombinantly expresses the human FSH receptor. CHO-FSHR cells were maintained in FSHR Growth media [MEM α(−) (Gibco, cat#12561-056)+ 10% dialyzed FBS (Gibco, cat#26300-020)+600 μg/ml Geneticin (Gibco, cat#10131-035)+0.02 μM MTX]. CHO-FSHR cells were seeded at $2 \times 10^4$ cells/well in 100 μl/well ($2 \times 10^6$ cells/10 ml=1 plate) and incubated at 37° C. for 24 hours prior to assay. Cells were used for assay if at least 70% confluent.

A 12-point serial 1:3 dilution was made starting at 67.5 nM for all samples and internal standard (Gonal F was used as an internal standard). All dilutions were made in assay media [DMEM/F12 (phenol free, Gibco, cat #11039-021)+1 mg/ml BSA (Sigma, A-6003)+0.1 mM IBMX (3-isobutyl-1-methylxanthone phosphodiesterase inhibitor, Sigma, cat#1-7018)]. Growth media was removed from the assay plate, 25 μl assay media (supplied with MA6000 cAMP MSD kit-Meso Scale Discovery, Gaithersburg, Md.) added, the plates recovered and incubated at 37° C. for 15 minutes. Wells were then dosed with 25 μl/well of the test sample, mixed, the plates recovered and incubated for 1 hour at 37° C. After the 1 hour incubation, the sample and media was removed from the wells. 25 μl of standard lysis buffer (supplied with MA 6000 Meso Scale Discovery kit) was then added to each well, the plates covered with plate sealer (Packard, cat#6005185) and shaken for 5 minutes. After the 5-minute lysis incubation, 25 μl of lysed cell material was transferred to the cAMP Meso Scale Discovery plate (supplied with MA6000 MSD kit) and incubated with gentle mixing at room temperature for 30 minutes. 25 μl of cAMP-AP conjugate was added to each well and mixed. 25 μl of anti-cAMP antibody was then added to each well, the plates covered with plate sealer and shaken for 30 minutes at room temperature. The plates were then washed six times with 350 μl/well of wash buffer on an automated plate washer. 100 μl of Sapphire II RTU (Ready-To-Use) substrate enhancer was then added to each well, the plates covered with plate sealer and incubate 30 minutes in the dark at 25° C. The plates were then read at one second per well with low levels of cAMP showing a high signal and high levels of cAMP showing a low signal. The dose-response curves of the FSH mutants are shown in FIG. 2. $EC_{50}$ values were calculated and shown in Table 2.

As shown in FIG. 2 and Table 2, each of the FSH mutants has in vitro activity comparable to that of wild-type FSH.

TABLE 2

| Sample | $EC_{50}$ M |
|---|---|
| FSH wild type | 2.16E−10 |
| Clone 10C- α GNRT/β GM1 | 2.58E−10 |
| Clone 11C- α GNFT/β GM1 | 2.78E−10 |

EXAMPLE 4

In Vivo Half-life of FSH Mutants

Two different lots of GNFT mutant and GNRT mutant, were analyzed in separate pharmacokinetic (PK) studies. The two studies were of the same design: 33 immature female SD rats 21-days-old (approx. 40 g body weight; Charles River Laboratories, Wilmington, Mass.) were randomly divided into 5 treatment groups (n=6) and 1 baseline group (n=3). The choice of immature female rats was based on the use of this age and sex for in vivo biological assessments of FSH activity. Animals in the treatment groups received subcutaneous (s.c.) injections of 4 ug of GM1 (control), GNFT mutant, GNRT mutant or 8 ug of Gonal-F rhFSH (control). Blood was collected from the retro-orbital sinus at 0 hr from the baseline group and at 1, 2, 4, 6, 10, 24, 48 and 72 hr from animals in the treatment groups (n=3/timepoint; rats were alternated so as not to be bled in 2 subsequent sampling points). Approximately 0.1 ml of blood was collected from each rat at each bleed, and plasma was harvested and stored at −80° C. until analyzed by ELISA. The assay used for measuring FSH proteins in serum from both studies was the DSL FSH Coated Well ELISA (Diagnostics Systems Laboratories, Webster, Tex.). Serum samples were each analyzed in triplicate.

The half-life of the GNFT mutant and GNRT mutant is approximately 17 hours whereas that of GM1 and Gonal-F controls is approximately 12 hr and 8 hr, respectively. This indicates that the GNFT mutant and GNRT mutants have a longer half-life than wild type FSH.

EXAMPLE 5

In Vivo Biological Activity

The in vivo model used to assess the biological activity of the GNRT and GNFT mutants is the rat ovarian weight gain assay. Treatment of immature 21 day old female rats with FSH or molecules with FSH-like activity, e.g. GNRT and GNFT mutants, triggers the growth of ovarian follicles and production of oocytes. This growth is easily detected by measurement of ovarian weight at the end of the treatment period. In the model, the substance to be tested is given by injection for three days and the ovaries are collected and weighed after the last dose. This assay was used for several decades as the basis for assigning FSH potency to clinical products for label purposes. It measures the relevant physiological action of FSH and has a clear correlation to performance of products in the clinic.

The in vivo activity of the GNRT and GNFT mutants was compared to that of wild-type FSH. All doses were defined based on predicted equivalence of FSH, taking into account the in vitro potency and the half-life in rats. The GNRT and GNFT mutants were found to possess potent FSH activity with a magnitude similar to that of wild-type FSH.

The invention claimed is:

1. An isolated mutant follicle stimulating hormone (FSH) comprising a β-subunit and an α-subunit, wherein the β-subunit comprises SEQ ID NO: 3 and the α-subunit comprises SEQ ID NO: 4 or 5.

2. The mutant FSH of claim 1, wherein from 0 to 6 asparagine residues are glycosylated.

3. The mutant FSH of claim 1, wherein the α-subunit comprises the sequence of SEQ ID NO: 5 and wherein N5 of this sequence is glycosylated.

4. The mutant FSH of claim 1, wherein the α-subunit comprises SEQ ID NO: 4.

5. A composition comprising a pharmaceutically acceptable carrier or excipient and a mutant (FSH) comprising a β-subunit and an α-subunit, wherein the β-subunit comprises SEQ ID NO: 3 and the α-subunit comprises SEQ ID NO: 4 or 5.

6. The composition of claim 5, wherein from 0 to 6 asparagine residues are glycosylated.

7. The composition of claim 5, wherein the α-subunit comprises the sequence of SEQ ID NO: 5 and wherein N5 of this sequence is glycosylated.

8. The composition of claim 5, wherein the α-subunit comprises SEQ ID NO: 4.

9. A method of stimulating folliculogenesis in a mammal comprising administering to a mammal in need thereof a composition of claim 5 in an amount sufficient to stimulate folliculogenesis.

10. A method of inducing ovarian hyperstimulation in a mammal comprising administering to a mammal in need thereof a composition of claim 5 in an amount sufficient to induce ovarian hyperstimulation.

* * * * *

UNITED STATES PATENT AND TRADEMARK OFFICE
CERTIFICATE OF CORRECTION

PATENT NO.        : 7,740,862 B2                                              Page 1 of 1
APPLICATION NO. : 12/096125
DATED             : June 22, 2010
INVENTOR(S)       : Marco Muda, Xuliang Jiang and Sean D. McKenna It is certified that error appears in the above-identified patent and that said Letters Patent is hereby corrected as shown below:

Column 2,
Line 34, "the P-subunit" should read --the β-subunit--.

Column 3,
Line 4, "hCG α-subunit" should read --hCG β-subunit--.

Signed and Sealed this

Twenty-first Day of September, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 92
<212> TYPE: PRT
<213> ORGANISM: Homs sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 111
<212> TYPE: PRT
<213> ORGANISM: Homo sapiens

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 3
<211> LENGTH: 111
<212> TYPE: PRT
<213> ORGANISM: Artificial
<220> FEATURE:
<223> OTHER INFORMATION: beta subunit mutant E55N/V57T

<400> SEQUENCE: 3

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Asn Leu Thr Tyr Glu Thr Val Arg Val Pro

-continued

```
                    50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
                    85                  90                  95

Arg Gly Leu Gly Pro Ser Tyr Cys Ser Phe Gly Glu Met Lys Glu
                   100                 105                 110

<210> SEQ ID NO 4
<211> LENGTH: 96
<212> TYPE: PRT
<213> ORGANISM: Artificial
<220> FEATURE:
<223> OTHER INFORMATION: alpha subunit insertion mutant GNFT

<400> SEQUENCE: 4

Ala Pro Asp Gly Asn Phe Thr Val Gln Asp Cys Pro Glu Cys Thr Leu
  1               5                  10                  15

Gln Glu Asn Pro Phe Phe Ser Gln Pro Gly Ala Pro Ile Leu Gln Cys
                 20                  25                  30

Met Gly Cys Cys Phe Ser Arg Ala Tyr Pro Thr Pro Leu Arg Ser Lys
             35                  40                  45

Lys Thr Met Leu Val Gln Lys Asn Val Thr Ser Glu Ser Thr Cys Cys
         50                  55                  60

Val Ala Lys Ser Tyr Asn Arg Val Thr Val Met Gly Gly Phe Lys Val
 65                  70                  75                  80

Glu Asn His Thr Ala Cys His Cys Ser Thr Cys Tyr Tyr His Lys Ser
                 85                  90                  95

<210> SEQ ID NO 5
<211> LENGTH: 96
<212> TYPE: PRT
<213> ORGANISM: Artificial
<220> FEATURE:
<223> OTHER INFORMATION: alpha subunit insertion mutant GNRT

<400> SEQUENCE: 5

Ala Pro Asp Gly Asn Arg Thr Val Gln Asp Cys Pro Glu Cys Thr Leu
  1               5                  10                  15

Gln Glu Asn Pro Phe Phe Ser Gln Pro Gly Ala Pro Ile Leu Gln Cys
                 20                  25                  30

Met Gly Cys Cys Phe Ser Arg Ala Tyr Pro Thr Pro Leu Arg Ser Lys
             35                  40                  45

Lys Thr Met Leu Val Gln Lys Asn Val Thr Ser Glu Ser Thr Cys Cys
         50                  55                  60

Val Ala Lys Ser Tyr Asn Arg Val Thr Val Met Gly Gly Phe Lys Val
 65                  70                  75                  80

Glu Asn His Thr Ala Cys His Cys Ser Thr Cys Tyr Tyr His Lys Ser
                 85                  90                  95
```